United States Patent [19]

Goto et al.

[11] Patent Number: 4,839,091
[45] Date of Patent: Jun. 13, 1989

[54] TOLAN DERIVATIVE AND LIQUID CRYSTAL COMPOSITION CONTAINING THE SAME

[75] Inventors: Yasuyuki Goto, Ichihara; Tetsuya Ogawa, Futtsu, both of Japan

[73] Assignee: Chisso Corporation, Japan

[21] Appl. No.: 205,286

[22] Filed: Jun. 10, 1988

[30] Foreign Application Priority Data

Jun. 13, 1987 [JP] Japan .................. 62-147796

[51] Int. Cl.$^4$ ............. C09K 19/30; C09K 19/54; C07C 25/24
[52] U.S. Cl. .............. 252/299.63; 252/299.5; 570/128; 350/350 R
[58] Field of Search ........... 252/299.5, 299.6, 299.63; 570/128; 350/350 R

[56] References Cited

U.S. PATENT DOCUMENTS

| | | | |
|---|---|---|---|
| 4,695,398 | 9/1987 | Goto et al. | 252/299.5 |
| 4,713,468 | 12/1987 | Takatsu et al. | 252/299.63 |
| 4,764,636 | 8/1988 | Sasaki et al. | 560/102 |
| 4,778,620 | 10/1988 | Goto et al. | 252/299.63 |
| 4,788,363 | 11/1988 | Takatsu et al. | 252/299.63 |

FOREIGN PATENT DOCUMENTS

| | | |
|---|---|---|
| 276067 | 7/1988 | European Pat. Off. . |
| 60-155142 | 8/1985 | Japan . |
| 61-260031 | 11/1986 | Japan . |
| 62-103031 | 5/1987 | Japan . |
| 88/02130 | 3/1988 | PCT Int'l Appl. ............ 252/299.61 |
| 2155465 | 9/1985 | United Kingdom . |

*Primary Examiner*—Teddy S. Gron
*Assistant Examiner*—J. E. Thomas
*Attorney, Agent, or Firm*—Leydig, Voit & Mayer

[57] ABSTRACT

A liquid crystal substance having a large optical anisotropy value, a low viscosity and a superior compatibility with other liquid crystal compounds at low temperatures and also raising the degree of choice of liquid crystal materials and a liquid crystal composition containing the above substance are provided, which substance is a 4-(trans-4-alkylcyclohexyl)-3',4'-difluorotolan expressed by the formula

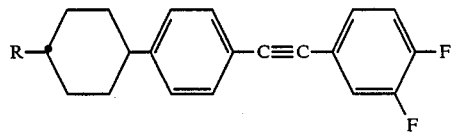

wherein R represents an alkyl group of 1 to 10 carbon atoms.

7 Claims, No Drawings

TOLAN DERIVATIVE AND LIQUID CRYSTAL COMPOSITION CONTAINING THE SAME

BACKGROUND OF THE INVENTION

1. Field of the Invention

This invention relates to a novel tolan derivative and a liquid crystal composition containing the same.

2. Description of the Related Art

Display elements applying liquid crystals utilize various electrooptical effects of liquid crystal substances, and the display mode thereof include various modes such as TN (Twisted Nematic) mode, DS (Dynamic Scattering) mode, guest-host mode, DAP mode (Dynamic Scattering), etc. The properties required for liquid crystals used according to these modes vary, respectively, but it has been required in common to the modes that the liquid crystals exhibit liquid crystal phases within a temperature range as broad as possible and they are stable to moisture, heat, air, etc. At present, however, there is no single compound which satisfies all such requirements and hence there have been used liquid crystal compositions obtained by mixing several kinds of liquid crystal compounds with each other or by mixing several liquid crystal compounds with compounds similar to liquid crystals.

As examples of tolan derivatives used as a component of liquid crystal materials, compounds expressed by the following formulas are disclosed in (1) Japanese patent application laid-open No. Sho 60-155142/1985 and (2) Japanese patent application laid-open No. Sho 61-260031/1986, respectively:

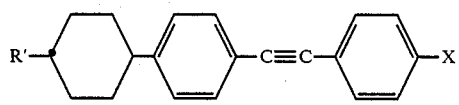
(1)

wherein R' represents an alkyl group and X represents a halogen atom, and

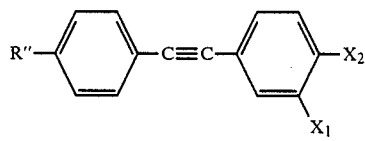
(2)

wherein R'' represents an alkyl group; $X_1$ represents a hydrogen atom or a halogen atom; and $X_2$ represents a halogen atom. These tolan compounds are liquid crystal materials characterized by having a halogen atom(s) as a substituent and also having a large optical anisotropy value (hereinafter abbreviated to $\Delta n$).

Among the compounds, the compound of the formula (1) has a relatively high clearing point, but has a low compatibility with other liquid crystal compounds at low temperatures so that crystals are deposited and hence it has a drawback of being impossible to make the best use of its specific features. The compound of the formula (2) has no liquid crystal phase; hence when it is used as a component of liquid crystal compositions, it has a drawback of making the N-I point of the compositions too low.

SUMMARY OF THE INVENTION

The object of the present invention is to provide a liquid crystal substance having a large $\Delta n$, a low viscosity and a superior compatibility with other liquid crystal compounds at low temperatures and also to raise the degree of choice of liquid crystal materials.

The present invention resides in a 4-(trans-4-alkylcyclohexyl)-3',4'-difluorotolan expressed by the formula

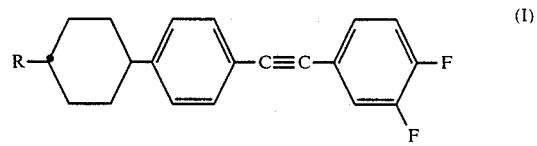
(I)

wherein R represents an alkyl group of 1 to 10 carbon atoms, and a liquid crystal composition containing the above compound.

DETAILED DESCRIPTION OF PREFERRED EMBODIMENTS

Examples of the tolan derivatives provided by the present invention are as follows:

4-(trans-4-methylcyclohexyl)-3',4'-difluorotolan
4-(trans-4-ethylcyclohexyl)-3',4'-difluorotolan
4-(trans-4-propylcyclohexyl)-3',4'-difluorotolan
4-(trans-4-butylcyclohexyl)-3',4'-difluorotolan
4-(trans-4-pentylcyclohexyl)-3',4'-difluorotolan
4-(trans-4-hexylcyclohexyl)-3',4'-difluorotolan
4-(trans-4-heptylcyclohexyl)-3',4'-difluorotolan
4-(trans-4-octylcyclohexyl)-3',4'-difulorotolan
4-(trans-4-nonylcyclohexyl)-3',4'-difluorotolan
4-(trans-4-decylcyclohexyl)-3',4'-difluorotolan The compound of the formula (I) of the present invention may be prepared for example through the following route:

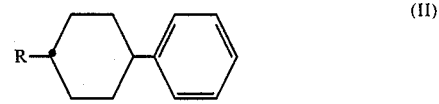
(II)

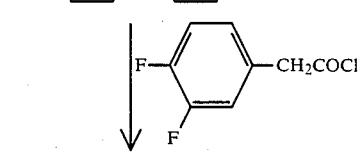
(III)

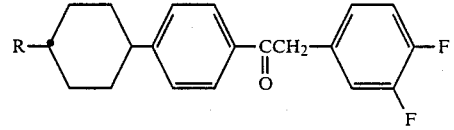
(IV)

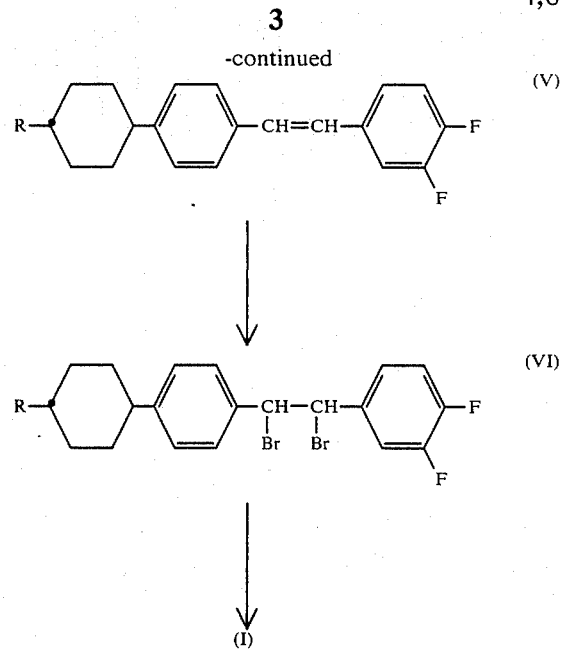

A trans-4-alkylcyclohexylbenzene is first reacted with 3,4-difluorophenylacetyl chloride of the formula (II) and anhydrous aluminum chloride in carbon disulfide to obtain a ketone derivative of the formula (III), followed by reacting this compound of the formula (III) with a reducing agent such as lithium aluminum hydride in anhydrous ether or anhydrous tetrahydrofuran to obtain a compound of the formula (IV) and successively subjecting this alcohol derivative to dehydration reaction in an inert organic solvent, in the presence of a catalyst mentioned later, under the atmospheric pressure and at a reflux temperature to obtain an ethylene derivative of the formula (V). As the inert organic solvent, benzene, toluene, chloroform, carbon tetrachloride, methylene chloride, etc. are suitable. As the catalyst, Lewis acids such as aluminum chloride, tin tetrachloride, titanium tetrachloride, etc., mineral acids such as sulfuric acid, hydrochloric acid, phosphoric acid, etc., toluenesulfonic acid, etc. may be used.

Bromine is then added to the above compound of the formula (V) in a solvent such as methylene chloride, ethylene chloride, carbon tetrachloride, etc. to obtain a compound of the formula (VI), followed by reacting the compound with a base such as potassium t-butoxide, and successively carrying out a series of purification operations such as extraction, washing, recrystallization, etc. to prepare the objective compound of the formula (I).

The 4-(trans-4-alkylcyclohexyl)-3',4'-difluorotolan of the present invention has the following specific features:
(i) its $\Delta n$ is large;
(ii) its viscosity is very low for a compound having a three-ring structure; and
(iii) its clearing point is high and its nematic temperature region is broad.

Among the compounds of the present invention, those which R in the formula (I) represents ethyl group, propyl group, butyl group or pentyl group are preferred. For example, 4-(trans-4-propylcyclohexyl)-3',4'-difluorotolan shown in Examples 1 and 4, mentioned later, is a liquid crystal compound having a $\Delta n$ as large as about 0.23, a viscosity as low as 32 cp in terms of a viscosity extrapolation value of 20° C., a broad nematic temperature range and a good stability and also it is a liquid crystal material having various well balanced specific features.

Representative examples of preferred liquid crystal compounds used as a component of the liquid crystal composition of the present invention in admixture with the compound of the formula (I) are 4-substituted-benzoic acid 4'-substituted-phenyl esters, 4-substituted-cyclohexanecarboxylic acid 4'-substituted-phenyl esters, 4-substituted-cyclohexanecarboxylic acid 4''-substituted-biphenylyl esters, 4-(4-substituted-cyclohexanecarbonyloxy)benzoic acid 4'-substituted-phenyl esters, 4-(4-substituted-cyclohexyl)benzoic acid 4'-substituted-cyclohexyl esters, 4,4'-substituted-biphenyls, 4,4'-substitutedphenylcyclohexanes, 4,4'-disubstituted bicyclohexanes, 4,4''-substituted-terphenyl, 4,4''-substituted-biphenylylcyclohexanes, 2-(4'-substituted-phenyl)-5-substituted-pyrimidines, etc.

In order to prevent occurrence of an interference fringe on the surface of liquid display cells which damages the cell appearance, it is necessary to adjust the product of the optical anisotropy ($\Delta n$) of liquid crystal materials placed in a cell of a particular cell thickness (d $\mu$m) to a specified value. In the case of display cells used in, since the value of $\Delta n \times d$ is set to any one of 0.5, 1.0, 1.6 and 2.2, use of a liquid crystal material having a large $\Delta n$ value makes it possible to reduce the d value. Reduction in the d value makes it possible to reduce the response time. Thus, a liquid crystal material having a large $\Delta n$ value is important for preparing a liquid crystal cell having a high response rate without any interference infringe. In order to reduce the response time, a low viscosity is also necessary. The compound of the formula (I) of the present invention is a novel nematic liquid crystal compound having a large $\Delta n$, a high N-I transition point and also a low viscosity; hence when the compound of the formula (I) of the present invention is mixed with various mother liquid crystals, it is possible to prepare a practical liquid crystal material having a low viscosity, a large $\Delta n$ and a high N-I transition point.

Namely, as shown in examples provided later, the tolan derivative compound of the formula (I) is effective for minimizing increasing of the viscosity, for raising the N-I point of mother liquid crystals up to a practically sufficient value, and for further raising $\Delta n$ value.

The present invention will be described in more detail by way of examples, but it should not be construed to be limited thereto. The symbols C-N point, S-N point and N-I point referred to in the examples mean crystalline-nematic phase transition point, smectic-nematic phase transition point and nematic-isotropic liquid phase transition point, respectively.

EXAMPLE 1

4-(Trans-4-propylcyclohexyl)-3',4'-difluorotolan

Anhydrous aluminum chloride (16.0 g, 0.12 mol) was added to carbon disulfide (100 ml), followed by adding 3,4-difluorophenylacetyl acid chloride (15.3 g, 0.1 mol) under cooling (0° to 5° C.), successively adding trans-4-propylcyclohexylbenzene (21 g, 0.1 mol), then agitating the reaction mixture at about 20° C. for 10 hours, distilling off carbon disulfide, adding the residue to a dilute hydrochloric acid aqueous solution, agitating the mixture for one hour to decompose an aluminum chloride complex, extracting deposited raw crystals with toluene (50 ml), washing the toluene extract with water, drying the water-washed toluene solution, distilling off toluene from the solution and recrystallizing the residual solids from ethyl acetate to obtain the following compound (23.6 g):

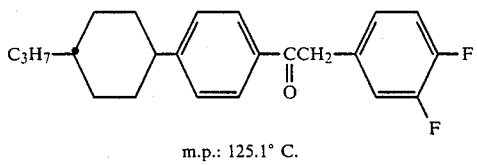

m.p.: 125.1° C.

This compound (23.6 g) was dissolved in anhydrous tetrahydrofuran (200 ml), followed by dropwise addition of the solution to a mixed solution of lithium aluminum hydride (1.3 g) with anhydrous tetrahydrofuran (50 ml), further agitating the mixture at 0° C. for 2 hours, adding to the reaction mixture, 20% sulfuric acid (50 ml) to dissolve inorganic substances, extracting a separated oily substance with toluene (100 m), washing the separated toluene solution with 10% $NaHCO_3$ aqueous solution, further washing it with water until the washing water became neutral, drying the toluene solution over anhydrous sodium sulfate, adding p-toluenesulfonic acid (1.0 g), refluxing the mixture on heating, removing the resulting formed water to the outside of the system, allowing the resulting toluene solution to cool down to room temperature, washing it with water until the washing water became neutral, drying it over anhydrous sodium sulfate and recrystallizing from ethyl acetate to obtain the following compound (16.0 g):

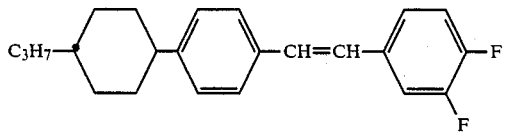

This compound had phase transition temperatures of C-N point: 96.3° C. and N-I point: 177.7° C.

This compound (16 g) was dissolved in methylene chloride (150 ml), followed by dropwise addition of bromine (7.3 g, 0.045 mol) to the solution, reacting the mixture with stirring for one hour, distilling off methylene chloride from the reaction mixture and recrystallizing the remaining solids from benzene (50 ml) to obtain the following objective compound (15.0 g).

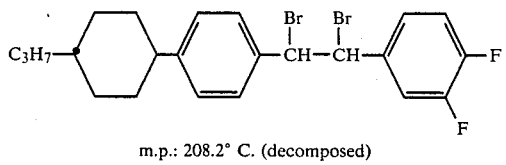

m.p.: 208.2° C. (decomposed)

This compound was then dissolved in anhydrous tetrahydrofuran (200 ml) at room temperature, followed by adding potassium t-butoxide (13.4 g, 0.12 mol), agitating the mixture at 40° C. for 2 hours, adding water (400 ml) to the reaction mixture, extracting the separated organic layer with toluene (100 ml), water-washing, drying, distilling off toluene and recrystallizing the remaining solids from ethyl acetate (20 ml) to obtain the following objective compound (9.8 g):

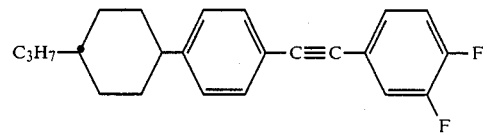

This compound had phase transition temperatures of C-N point: 87.5° C. and N-I point: 151.2° C.

EXAMPLE 2

The following compounds were prepared in the same manner as in Example 1:
4-(trans-4-ethylcyclohexyl)-3',4'-difluorotolan C-N point: 66.5° C., N-I point: 129.0° C.
4-(trans-4-pentylcyclohexyl)-3',4'-difluorotolan C-N point: 72.5° C., S-N point: 45.0° C., (monotropic) N-I point: 155.4° C.

EXAMPLE 3

A liquid crystal composition A consisting of
trans-4-propyl-(4-cyanophenyl)cyclohexane 30% by weight
trans-4-pentyl-(4-cyanophenyl)cyclohexane 40% by weight
trans-4-heptyl-(4-cyanophenyl)cyclohexane 30% by weight
has a N-I point of 52.1° C., a viscosity of 22.4 cp at 20° C. and an optical anisotropy Δn of 0.119. A liquid crystal composition obtained by adding a compound of the present invention, 4-(trans-4-propylcyclohexyl)-3',4'-difluorotolan shown in Example 1 (15 parts by weight) to the above liquid crystal composition (85 parts by weight) had a N-I point raised to 61.2° C., a viscosity slightly increased to 23.2 cp and an optical anisotropy Δn increased to 0.138.

EXAMPLE 4

A liquid crystal composition obtained by adding a compound of the present invention, 4-(trans-4-ethylcyclohexyl)-3',4'-difluorotolan, shown in Example 2, (15 parts by weight) to the above liquid crystal composition A used in Example 3 (85 parts by weight) had a N-I point of 57.9° C., a viscosity of 23.4 cp at 20° C. and an optical anisotropy, Δn, of 0.131.

EXAMPLE 5

A liquid crystal composition obtained by adding 4-(trans-4-pentylcyclohexyl)-3',4'-difluorotolan, shown in Example 2, (15 parts by weight) to the above liquid crystal composition A, used in Example 3, (85 parts by weight) had a N-I point of 62.3° C., a viscosity of 23.6 cp at 20° C. and an optical anisotropy Δn of 0.136.

COMPARATIVE TEST

In order to compare the specific features of the tolan derivatives expressed above by the formulas (1) and (2) with those of the tolan derivatives of the present invention, the following tests were carried out:

Four kinds of compounds to be compared, each in 15 parts by weight, were respectively mixed with the liquid crystal composition A used in Example 3 (85 parts by weight) to prepare four compositions. Each of these 4 compositions and the composition A were filled in a TN cell of 10 μm thick and the operating threshold voltages (Vth) of the resulting cells were measured. Further, these compositions were stored in a refrigerator at $-30°$ C. for 10 days and the presence or absence of crystal deposition was observed. The results of the Comparative tests are shown in Table 1. In the column of low temperature compatibility, a symbol o indicates no deposition of crystals and a symbol x indicates deposition of crystals.

Further, the extrapolation values of dielectric anisotropy value ($\Delta\epsilon$) and the extrapolation values of viscosity ($\eta_{20}$) of the compounds to be compared are shown in the Table 1.

wherein R represents an alkyl group of 1 to 10 carbon atoms.

2. A 4-(trans-4-alkylcyclohexyl)-3',4'-difluorotolan according to claim 1 wherein said R is an alkyl group having 1 to 5 carbon atoms.

3. 4-(Trans-4-pentylcyclohexyl)-3',4'-difluorotolan.
4. 4-(Trans-4-butylcyclohexyl)-3',4'-difluorotolan.
5. 4-(Trans-4-propylcyclohexyl)-3',4'-difluorotolan.
6. 4-(Trans-4-ethylcyclohexyl)-3',4'-difluorotolan.
7. A liquid crystal composition comprising at least

TABLE 1

| No of composition | Compounds to be compared | Vth (V) | Low temperature compatibility | Extrapolation value of $\Delta\epsilon$ | Extraporation value of $\eta_{20}$ (cp) |
|---|---|---|---|---|---|
| 1 | $C_3H_7$—⟨⟩—C≡C—⟨⟩—F, F | 1.81 | o | 6.8 | 26.5 |
| 2 | $C_3H_7$—⟨⟩—⟨⟩—C≡C—⟨⟩—F | 1.92 | x | 5.6 | 28.2 |
| 3 | $C_3H_7$—⟨⟩—⟨⟩—C≡C—⟨⟩—F, F | 1.50 | o | 9.4 | 27.7 |
| 4 | $C_5H_{11}$—⟨⟩—⟨⟩—C≡C—⟨⟩—F, F | 1.52 | o | 8.5 | 30.4 |
| A | — | 1.58 | o | 10.7 | 22.4 |

What we claim is:

1. A 4-(trans-4-alkylcyclohexyl)-3',4'-difluorotolan expressed by the formula

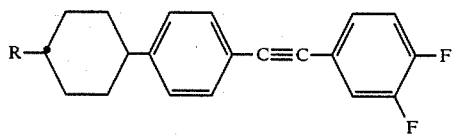

wherein R represents an alkyl group of 1 to 10 carbon atoms.

two components at least one of which is a 4-(trans-4-alkylcyclohexyl)-3',4'-difluorotolan expressed by the formula

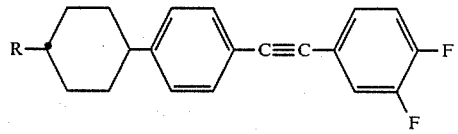

wherein R represents an alkyl group of 1 to 10 carbon atoms.

* * * * *